United States Patent [19]
Bennett

[11] 3,952,580
[45] Apr. 27, 1976

[54] APPARATUS FOR COUNTING PARTICLE CONTAMINATION IN A LIQUID

[75] Inventor: Milton C. Bennett, Moline, Ill.

[73] Assignee: J. I. Case Company, Racine, Wis.

[22] Filed: June 19, 1975

[21] Appl. No.: 588,406

[52] U.S. Cl. .............................. 73/61.4; 324/71 CP
[51] Int. Cl.² .......................................... G01N 15/00
[58] Field of Search ............. 73/61.4, 61 R, 432 PS; 324/71 CP

[56] References Cited
UNITED STATES PATENTS 3,800,220   3/1974   Thoma ............................ 324/71 CP

*Primary Examiner*—Richard C. Queisser
*Assistant Examiner*—Joseph W. Roskos
*Attorney, Agent, or Firm*—Arthur J. Hansmann

[57] ABSTRACT

Apparatus for counting particle contamination in a liquid and including a hydraulic cylinder for receiving the liquid and having mechanism for forcing the cylinder piston to exhaust the liquid from the cylinder and into a sensor where the particles are counted. The apparatus includes electric switches connected to the sensor and responsive to the position of the cylinder rod for setting the sensor in various positions for counting. Also, liquid lines are connected with the sensor, and valves are used for directing the liquid to the cylinder and the sensor, and a line restrictor creates the desired pressure in the fluid. The apparatus may receive the liquid from several lines, through a dispensing valve, or it may receive the liquid from a special container.

9 Claims, 2 Drawing Figures

U.S. Patent  April 27, 1976  3,952,580
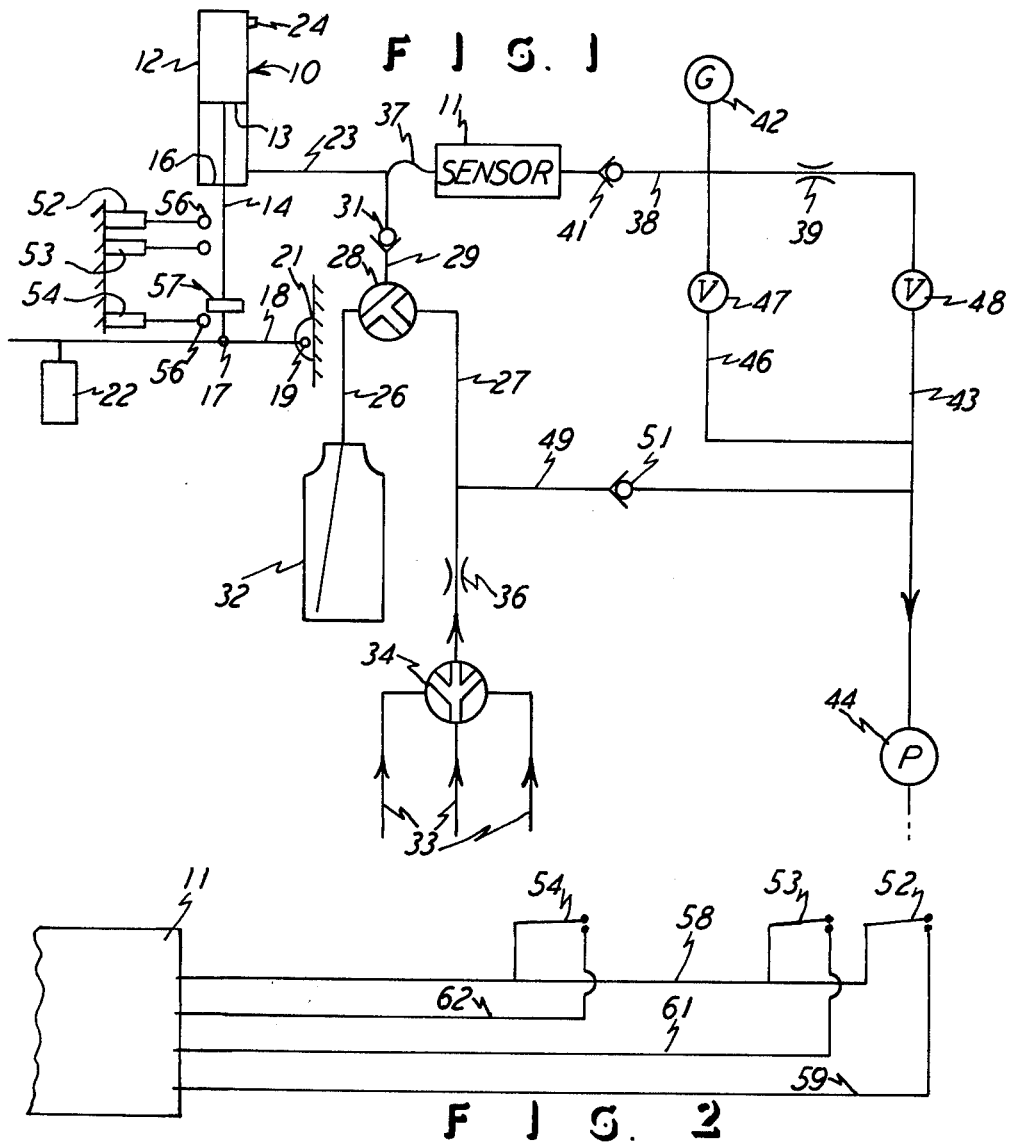

APPARATUS FOR COUNTING PARTICLE CONTAMINATION IN A LIQUID

This invention relates to apparatus for counting particle contamination in a liquid, and, more particularly, it includes a cylinder which receives a charge of the liquid and dispenses the charge to a sensor which counts the particles, and electric switches are actuated by movement of the cylinder rod, and the switches are connected to the sensor for electrically controlling the sensor according to the position of the cylinder rod.

BACKGROUND OF THE INVENTION

Industry has recently become more aware of and concerned with contamination control in liquids, such as hydraulic fluids. In this regard, particle counters have been employed for analyzing the hydraulic fluid and determining the amount of particle contamination in the fluid, and conventional sensors are available for the purpose mentioned. However, the sensors that are presently available are designed primarily for laboratory use, and their operation is not fast enough for production line use, and the available equipment requires an expert operator whose skills are beyond those of the usual production personnel. Also, to use present-day particle counters directly in a production system presents a problem in obtaining an accurate count since the system normally has pressure variations, and the sensors are sensitive to pressure variations and pulsations and thus give inaccurate counts.

Accordingly, it is a primary objective of this invention to provide apparatus for counting particle contamination in a liquid and to obtain an accurate count of the particles even though the apparatus is connected with the liquid lines in an industrial installation. Further, the aforementioned objective is accomplished even where the apparatus is not directly connected to the industrial installation, but only a specimen of the liquid is obtained from the industrial liquid line and is fed into the apparatus of this invention, all for obtaining an accurate particle count.

More particularly, it is the result and objective of this invention to provide apparatus for counting particle contamination in a liquid, wherein the apparatus creates and maintains a uniform pressure on the liquid being analyzed, and thus the accurate particle count is obtained. Still further, the aforementioned objectives and advantages are accomplished through reliable and available and easily operated apparatus, such that the apparatus can be readily and easily provided, and even a nonskilled or untrained person can operate the apparatus and obtain an accurate particle count. Still further, the apparatus of this invention permits the analysis of the multiplicity of specimens and with each specimen being subjected to the same pressure so that the apparatus will accurately operate on each specimen and the operation and end results and time of each test will be related to each other.

Still further, the prior art particle counter systems commonly utilize low pressure air to force the liquid through the sensor, and this is done generally at a maximum of approximately 30 psi. The present invention operates without the need for an air supply, and the system is easily provided and arranged to create a pressure of 100 psi which significantly reduces the size of entrained air bubbles in the liquid, and such air bubbles commonly create a counting error since the conventional sensor will respond to the presence of air bubbles.

Still further, it is an object of this invention to provide apparatus for counting particle contamination in a liquid, and wherein the apparatus is automatic in creating the desired pressure in the liquid being analyzed and in actuating switches which are electrically connected to the sensor so that the sensor is automatically positioned in a reset and a start and a stop condition, all as desired.

Other objects and advantages will become apparent upon reading the following description in light of the accompanying drawings.

BRIEF DESCRIPTION OF THE DRAWINGS

FIG. 1 is a view of the apparatus of this invention, and showing the schematic relationship of the various elements.

FIG. 2 is a wiring diagram of the switches and the sensor of FIG. 1.

DETAILED DESCRIPTION OF THE PREFERRED EMBODIMENT

The drawings show the apparatus to include the components of a cylinder assembly 10, a particle sensor 11, and the connecting liquid lines or hoses and the valves and switches and restrictor and pump and the like. That is, the cylinder assembly 10 includes a cylinder 12 and a piston 13 and a piston rod 14 extending from the cylinder 12, in any conventional fluid-tight manner through the cylinder end wall 16. The rod 14 is articularly connected at a suitable connection 17 to a lever 18 which is pivoted at 19 on a fixed mounting 21, in any conventional arrangement. The lever 18 extends from the mounting 21 and a weight 22 is suspended from the extending end of the lever 18, as seen in FIG. 1. Thus, pivotal action of the lever 18 is in accordance with up-and-down or axial movement of the rod 14, and thus the cylinder 10 can fluid-tightly receive a charge or specimen of the liquid to be analyzed, and that specimen can enter the cylinder 12 through a hose or liquid line 23. An air vent 24 on the upper end of the cylinder 12 permits the up-and-down movement of the piston 13 in the cylinder 12.

The liquid specimen can be introduced into the cylinder 12 through the liquid line or hose 26 or the line or hose 27, both of which are connected with a three-way valve 28 which is connected with the line 23 through a hose or line 29. A check valve 31, of a conventional arrangement, permits the liquid to flow from the valve 28 and into the line 23, but of course it prevents the flow in the opposite direction.

Thus, the lines 26 and 27 are respectively supplied with the liquid specimen to be analyzed, and line 26 is in fluid-flow communication with an open container 32 which may have the liquid specimen taken from any source desired, and thus the liquid from the container 32 is directed to the cylinder assembly 10 in a manner hereinafter described. Also, a liquid specimen could be presented in the line 27 which is supplied by a plurality of other lines or hoses designated 33 which are connected with a four-way valve 34 which directs liquid from any one of the lines 33 and into the line 27, in a conventional arrangement of connecting the four lines and the four-way valve. Also, a flow restrictor 36 is connected with the line 27 and restricts the flow and pressure of the liquid moving through the line 27. Thus, the lines 33 can be tappings directly from an industrial installation having liquid lines for the operation of equipment and machinery and the like, and the lines 33 therefore provide a direct supply of a sample or specimen of the liquid to be analyzed by the apparatus of this invention.

The sensor 11 is connected in the system by means of a hose or line 37 in fluid-flow communication with the lines 23 and 29, as shown, but it will be understood that the pressure in the line 29 is minimized and regulated, and therefore the flow does not go directly from the line 29 and into the line 27 and the sensor 11, but instead the flow goes from the cylinder assembly 10, as hereinafter described. It will therefore be seen and understood that the three-way valve 28, being a conventional valve, can be positioned to direct the flow from either line 26 or 27, alternately, and into the line 29, and because the container 32 is open and not under pressure, and because there is a restrictor 36 is the line 27, there is no appreciable pressure in the line 29 to cause the liquid to be directed into the sensor 11, at this time. Also, the sensor 11 is of a conventional design and can be the standard type made by the Royco Instruments, Inc. of Menlo Park, California, and the valves 28 and 34 can be of the standard type made by the Parker Hannifn Brass Products Division of the Parker Hannifn Company, 300 Parker Dr., Otsego, Mich.

Accordingly, to charge the cylinder assembly 10 and to then subsequently present that liquid charge to the sensor 11, the operator will raise the lever 18, with its weight 22 attached thereto, and this will create a suction in the lower end of the cylinder 12, and thus the liquid will move from either line 26 or 27 and through the lines 29 and 23 and into the cylinder 12 as the piston 13 is raised through the pivoting of the lever 18, as mentioned. Release of the lever 18 then causes the weight 22 to bear downwardly on the rod 14 and thus create a pressure on the liquid in the lower end of the cylinder 12, and this action causes the liquid sample or specimen to be forced through the lines 23 and 37 and into the sensor 11, and such forcing creates a controlled and certain pressure on the liquid sample as it flows into and through the sensor 11, and thus the sensor can analyze the liquid flowing therethrough and thereby count the particles of contamination, all in a conventional manner of operation of the sensor 11. In order to create and maintain the pressure in the liquid flowing through the sensor 11, as mentioned, a liquid hose or line 38 extends from the sensor 11 and has a flow restrictor 39 therein to create the necessary fluid pressure in the sensor 11 and on the liquid therein. Also, a check valve 41 prevents backflow toward the sensor 11, and a pressure gauge 42, of a conventional design, is connected with the line 38 to observe the pressure in the line 38.

The liquid can flow through the line 38 and into a line 43 which further directs the flow to a pump 44 and back to any point desired, such as a reservoir or into the system from whence the lines 33 originated. Also, a bypass line 46, having a valve 47 therein, is connected with the lines 38 and 43 and permits purging of the system when the valve 47 is open to thereby pass the liquid from the line 38 and directly to the line 43, bypassing the restrictor 39. Then, in the test itself, the valve 47 is closed, and another 48, in the line 43 is open so that flow can go through the line 38 and directly to the line 43, as indicated.

The system also has another liquid line 49 which extends between the lines 27 and 43 and thus serves as a bypass such that liquid can go directly to the line 43 in the event that the pressure in the line 27 exceeds a pressure in the check valve 51 which is in the line 49. That is, the valve 51 can be of a conventional check valve type which permits flow only to the right in the line 49, as indicated, and the valve 51 can be selected and set so that it opens at 30 psi, for instance, and thus the pressure in the line 27 can never exceed 30 psi. Also, the gauge 42 can be such that it detects pressure between 0 and 400 psi. Therefore, the restrictor 39 creates the desired pressure in the liquid in the sensor 11, and it also creates the desired rate of flow through the sensor 11 so that the sensor can operate to accurately count the particle contamination. Further, with the system as shown, and with, for example, weight 22 being of a magnitude of 25 pounds on a certain cylinder assembly 10, a liquid pressure of 100 psi can be readily produced for presenting the liquid under the pressure to the sensor 11, all for the most efficient operation and accurate count.

The sensor 11 is of course of an electric type, of the nature mentioned, and three micro-switches 52, 53, and 54 are shown mounted adjacent the piston rod 14, and the switches have respective actuators 56 which are engaged by a shown protrusion 57 affixed to the rod 14 such that up-and-down movement of the rod 14, between points where the protrusion 57 is above the upper switch actuator 56 and the protrusion 57 can move to below the lowest switch actuator 56, and thereby the protrusion 57 will trip the three switches in sequence and at the times when the protrusion 57 is moving up or down with the up-and-down movement of the piston rod 14, as mentioned and as seen in FIG. 1. Thus, the switches can be of a standard type such as that made by the Micro-Switch Division of the Minneapolis-Honneywell Company of Freeport, Ill., and the switch 52 is a system reset switch and the switch 53 is a system start switch and the switch 54 is a system stop switch. Therefore, when the protrusion 57 is in its uppermost limit to engage the switch 52, then the system is reset to a commencing position, and, as the piston 13 and its rod 14 move downwardly to evacuate the charge into and through the sensor 11, the rod protrusion 57 will engage the start switch 53 and then control the flow of electric energy to the sensor 11 and thus commence the particle count, and that will continue until the rod protrusion 57 moves down to the lowest switch 54 which is then tripped and that stops the flow of electric energy to the sensor 11 and thus stops the counting of the particles by the sensor 11.

FIG. 2 shows a schematic arrangement of the switches 52 and 53 and 54 with a common electric line 58 connected thereto and with the return lines 59 and 61 and 62, respectively, connected to the electric sensor 11, all in a conventional arrangement. Of course when the operator again raises the lever 18, the three electric switches, and thus the sensor 11, will all be reset when the rod protrusion 57 engages the upper switch actuator 56, and at the same time a charge of the liquid is brought into the cylinder 12 for the analysis, all as mentioned above and as will be apparent to one skilled in the art. It will also be understood that with the arrangement described, and with the desired axial force applied downwardly on the rod 11, with the system shown and described, a desired and certain quantity of liquid will flow through the sensor 11, say 10 milliliters, between the time that the start switch 53 and stop switch 54 are respectively actuated, and thus the sensor 11 will actually give the particle count per milliliter of liquid, as desired. Thus, one type of the micro-switch shown and useful is the Honeywell BZ-2 RQ18-A, and there may of course be push-button switches which could be manually operated at the time that the rod 14 reaches certain positions, and that too is believed to be obvious to one skilled in the art, though that arrangement would take away from the automated nature of the switch portion of the apparatus described and shown herein. With this apparatus, an unskilled operator can monitor the apparatus and maneuver it to whatever extent is necessary, such as to lift the lever 18 for charging the system, as described. Also, the particular arrangement of the length of the lever 18 and the location of the connection to the rod 14, such as at 17, as described, and also the amount of the weight 22, can all be arranged so that the desired pressure and quantity of flow through the sensor 11 is achieved, all in a manner which will now be understood by one skilled in the art and in a manner which is readily and easily attainable. Thus, the cylinder 12 is disposed with its longitudinal axis upright, and the rod 14 is permitted to move in a direction along the axis of the cylinder 12, and therefore the connection 17 can be arranged to accommodate such true axial rod movement, such as by having the connection 17 slightly slideable along the lever 18 but yet arranged so that the size the protrusion 57 will engage the switch actuators 56; or, the rod 14 could be arranged fluid-tight with the cylinder 12 but yet accommodate a slight deviation of the rod 14 off the axis of the cylinder 12 and still retain the rod fluid-tight with the cylinder end 16, in any conventional arrangement of making a liquid seal between the rod 14 and the cylinder end 16 while permitting the rod deviation mentioned. Further, it will be seen that the apparatus readily accommodates either taking the liquid specimen directly from an industrial installation and through the lines 33, and thus returning the liquid to the installation through the line 43 and pump 44, or the apparatus can be used to present a specimen in the container 32 in which instance the specimen in the container 32 was taken from any source, as convenient. Also, the sensor 11 may be the model No. 345 made by Royco Instruments, Inc. of Menlo Park, Cal.

What is claimed is:

1. Apparatus for counting particle contamination in a liquid, comprising a hydraulic cylinder having a liquid outlet opening in one end thereof, a liquid inlet line connected with said cylinder for introducing into said cylinder a charge of the liquid to be examined, a liquid valve connected with said inlet line for controlling liquid flow through said inlet line, a piston and rod assembly operatively associated with said cylinder and movable therein and with the rod extending from said cylinder, mechanism attached to the extending end of said rod for applying a uniform force on the piston in the axial direction of said cylinder and from the other end thereof and toward said outlet opening for forcing liquid from said cylinder and out said outlet opening, a particle counter sensor, a liquid flow line connected between said cylinder outlet opening and said sensor for directing liquid from said cylinder to said sensor, and a liquid flow restrictor connected with said sensor and downstream therefrom for establishing a pressure in the liquid flowing from said cylinder and through said sensor, to thereby establish a liquid pressure and flow rate through said sensor to enable said sensor to count contamination particles in the liquid flowing therethrough.

2. The apparatus as claimed in claim 1, wherein said mechanism includes a weight operatively connected with said rod for applying the force on said piston.

3. The apparatus as claimed in claim 1, wherein said cylinder is disposed with its longitudinal axis upright, and said mechanism includes a lever pivotally mounted adjacent the lower end of said cylinder, and said mechanism includes a weight suspended on said lever for applying the force on said piston.

4. The apparatus as claimed in claim 1, including a system of liquid lines connected with said cylinder and said sensor and said restrictor and presenting a closed liquid system for tapping off the liquid in said system and directing it to said sensor and back to said system.

5. The apparatus as claimed in claim 1, wherein said sensor is electrically energized, and an electric switch disposed adjacent said piston rod and being operable by the axial movement of said rod to open and close said switch, and said switch and said sensor being electrically connected together for energizing said sensor in accordance with the axial movement of said piston rod.

6. The apparatus as claimed in claim 5, including a plurality of said electric switches disposed in a row adjacent said piston rod and being operable by the axial movement of said rod to open and close said switches, and said switches and said sensor being electrically connected together for controlling the energizing of said sensor in accordance with the axial movement of said rod.

7. The apparatus as claimed in claim 5, wherein said switches are disposed in their row in a sequence and are connected to said sensor to be sequentially a reset switch and start switch and stop switch actuated in the said sequence for obtaining an accurate count of contamination particles in the liquid flowing through said sensor from the time said rod actuates said start switch and until said rod actuates said stop switch.

8. The apparatus as claimed in claim 7, wherein said cylinder is disposed with its longitudinal axis upright, and said mechanism includes a lever pivotally mounted adjacent the lower end of said cylinder, and said mechanism includes a weight suspended on said lever for applying the force on said piston.

9. The apparatus as claimed in claim 1, including multiple liquid lines connected with said valve for selectively receiving liquid from various sources and directing it to said valve.

* * * * *